(12) United States Patent
DeCarvalho et al.

(10) Patent No.: US 6,974,892 B2
(45) Date of Patent: Dec. 13, 2005

(54) SANITARY NAPKIN

(75) Inventors: Antonio Carlos Ribeiro DeCarvalho, San Paulo (BR); Marcia Helena Teixeira Fajolli, Sao Paulo (BR)

(73) Assignee: Johnson & Johnson Industria E Comercio LTDA, Sao Jose Dos Campos-SP (BR)

( * ) Notice: Subject to any disclaimer, the term of this patent is extended or adjusted under 35 U.S.C. 154(b) by 289 days.

(21) Appl. No.: 10/287,142

(22) Filed: Nov. 4, 2002

(65) Prior Publication Data

US 2003/0100874 A1 May 29, 2003

(51) Int. Cl.⁷ ............................................. A61F 13/15
(52) U.S. Cl. ................ 604/380; 604/378; 604/385.01; 604/385.03; 604/385.04; 604/385.05; 604/386
(58) Field of Search ............................ 604/385.01, 380, 604/378, 385.21, 385.03, 385.04, 385.05, 604/386, 383

(56) References Cited

U.S. PATENT DOCUMENTS

| | | | |
|---|---|---|---|
| 1,948,626 A | | 2/1934 | Jurgensen |
| 3,430,630 A | | 3/1969 | Megison et al. |
| 4,184,498 A | | 1/1980 | Franco |
| 4,900,319 A | | 2/1990 | Richwine |
| 5,236,429 A | * | 8/1993 | Widlund ................ 604/390 |
| H001657 H | * | 6/1997 | Hammons et al. ..... 604/385.05 |

FOREIGN PATENT DOCUMENTS

| | | |
|---|---|---|
| CN | 1131386 A | 9/1996 |
| CN | 2319004 Y | 5/1999 |
| CN | 2360055 Y | 1/2000 |
| CN | 2376889 Y | 5/2000 |
| DE | 296 00 384 U1 | 6/1996 |
| DE | 299 11 806 U1 | 12/2000 |
| WO | WO 95/03022 A2 | 2/1995 |
| WO | WO 95/03023 A2 | 2/1995 |
| WO | WO 95/03024 A2 | 2/1995 |
| WO | WO 95/03025 A2 | 2/1995 |
| WO | WO 95/07675 A2 | 3/1995 |
| WO | WO 95/08311 A1 | 3/1995 |
| WO | WO 99/25290 A1 | 5/1999 |

* cited by examiner

Primary Examiner—Larry I. Schwartz
Assistant Examiner—Jacqueline F. Stephens

(57) ABSTRACT

A sanitary napkin having a first transverse end and an opposite second transverse end defining therebetween a length and a plurality of varying widths along its length, the widths being perpendicular to the length, including;
(i) a first width located substantially between ⅕ and ½ of the length as measured from the first transverse,
(ii) a second width located substantially from ⅕ to ½ of the length as measured from the second transverse end,
(iii) the first width being the maximum width of the absorbent portion, the second width being less than or equal to the first width; and
(iv) a central region intermediate the first width and the second width, the central region having a maximum width that is less than or equal to the first width.

7 Claims, 5 Drawing Sheets

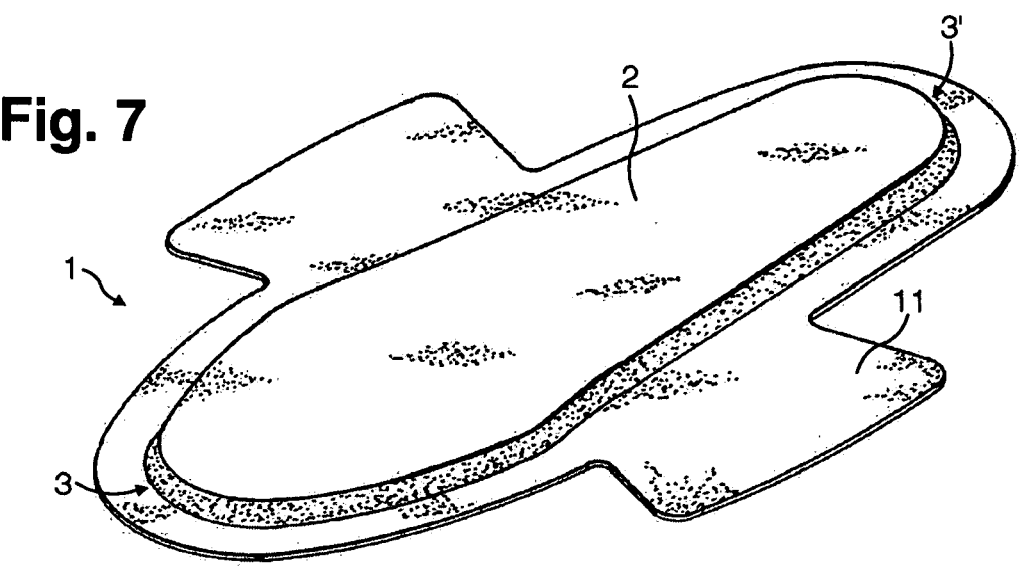
Fig. 7
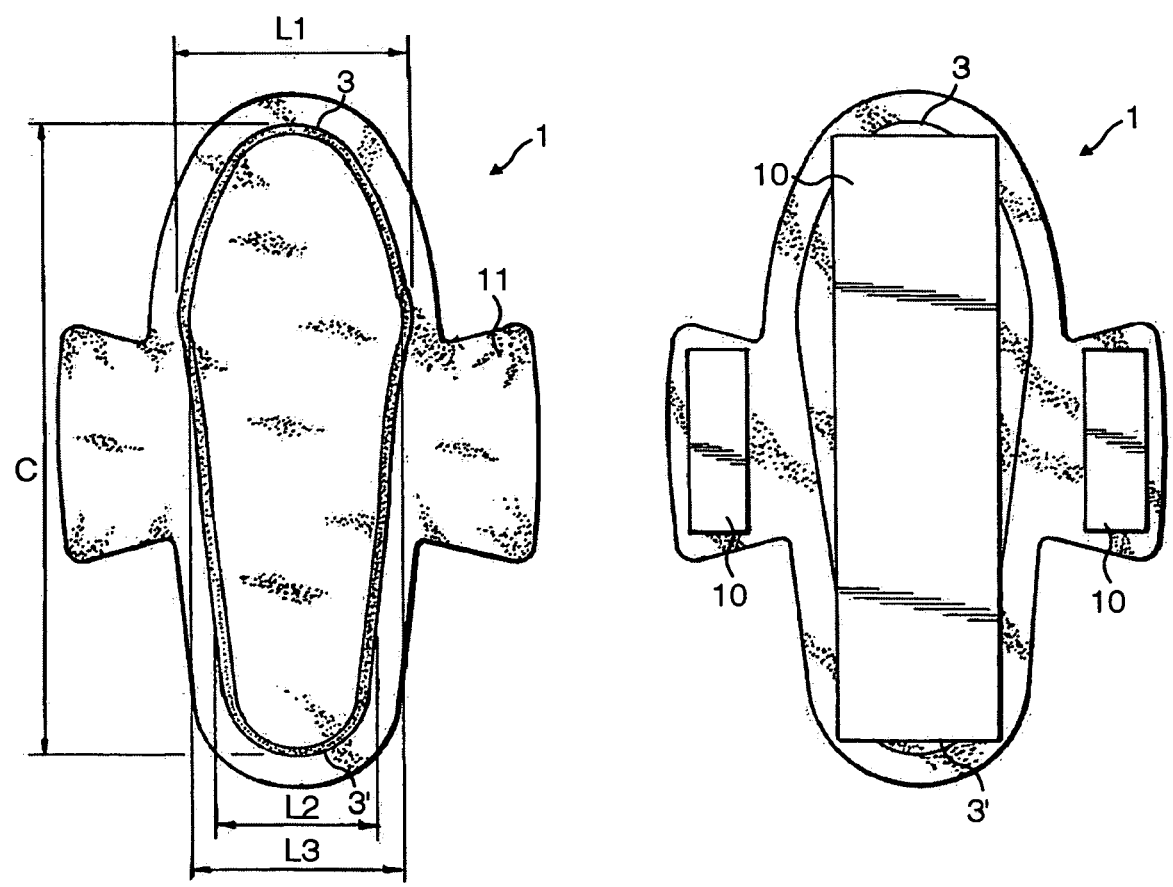
Fig. 8
Fig. 9

SANITARY NAPKIN

The present invention relates to a sanitary napkin for absorbent body exudates, such as menstrual fluids and urine, having enhanced comfort of use.

BACKGROUND OF THE INVENTION

It is generally known that conventional sanitary napkins have a substantially planar, elongated shape. While many older napkin shapes were substantially rectangular, having straight side edges, many newer designed sanitary napkins have been shaped to better fit the contours of a wearer's body such as in the form of an hourglass. These hourglass shaped sanitary napkins have absorbent portions wherein a maximum width is located in the product end regions, i.e. generally up to ⅙ of its length as measured inward from the distal end of the napkin. However, these napkins have been found to have several shortcomings, described as follows:

Firstly, these napkins are inefficient since they have a greater amount of absorbent material in the end regions of the sanitary napkin, which are regions where leakage rarely occur, and a lesser amount of absorbent material in a central region that is adapted to be worn between the wearer's legs.

Secondly, the excess material in the end regions and the absence of material in the region between the legs causes a deformation in the sanitary napkin, due to this material accumulation, causing discomfort of use and, which can lead to the leakage of body exudate.

SUMMARY OF THE INVENTION

It is an object of this invention to provide a sanitary napkin having an end region of substantially slender shape which provides comparable absorbent ability to conventionally shaped napkins and provides excellent comfort of use.

The objects of this invention are attained by a sanitary napkin, comprising an absorbent portion having a first transverse end and an opposite second transverse end defining therebetween a length, a first longitudinal side and an opposite second longitudinal side defining therebetween a width, the width varying along the length of the absorbent portion, wherein:

(i) a first width is located between ⅕ and less than ½ of the length of the absorbent portion as measured from the first transverse end, the first width being greater than any width of the absorbent portion located between the first transverse end and the first width;

(ii) a second width located substantially from ⅕ to less than ½ of the length of the absorbent portion as measured from the second transverse end, the second width being less than or equal to the first width;

(iii) a central region intermediate the first width and the second width, the central region having a maximum width that is less than or equal to the first width.

BRIEF DESCRIPTION OF THE DRAWINGS

This invention will be thereafter described in more details based on an example of execution represented in drawings. The figures have:

FIG. 7—is a perspective view of a third variation of the sanitary napkin object of this invention;

FIG. 8—is a top view of the napkin illustrated in FIG. 7;

FIG. 9—is a bottom view of the napkin illustrated in FIGS. 7 and 8;

DETAILED DESCRIPTION OF THE INVENTION

Figure 1:
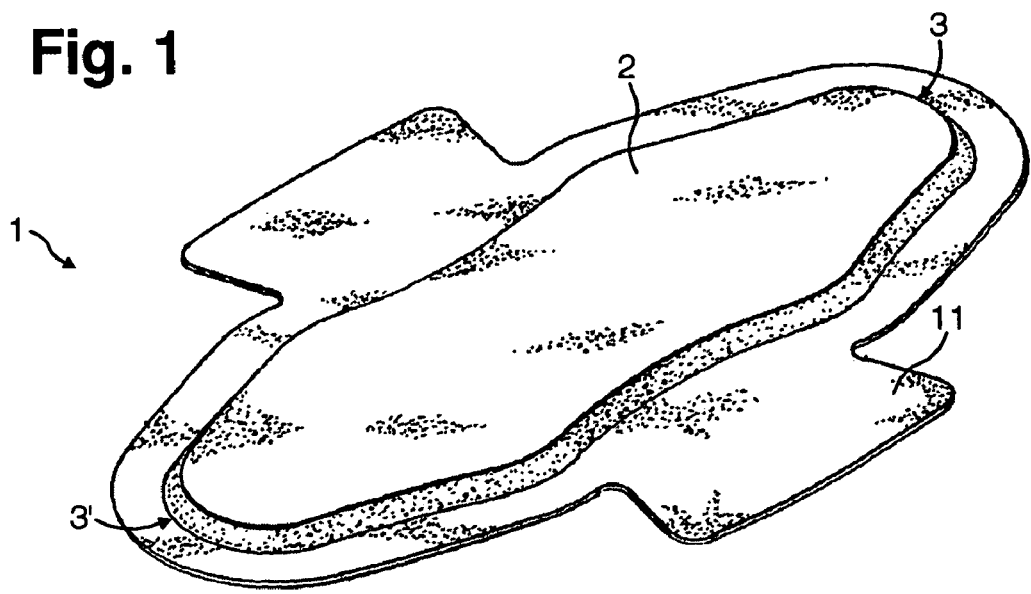
FIG. 1—is a perspective view of a first variation of the sanitary napkin object of this invention.
Figures 2, 3:
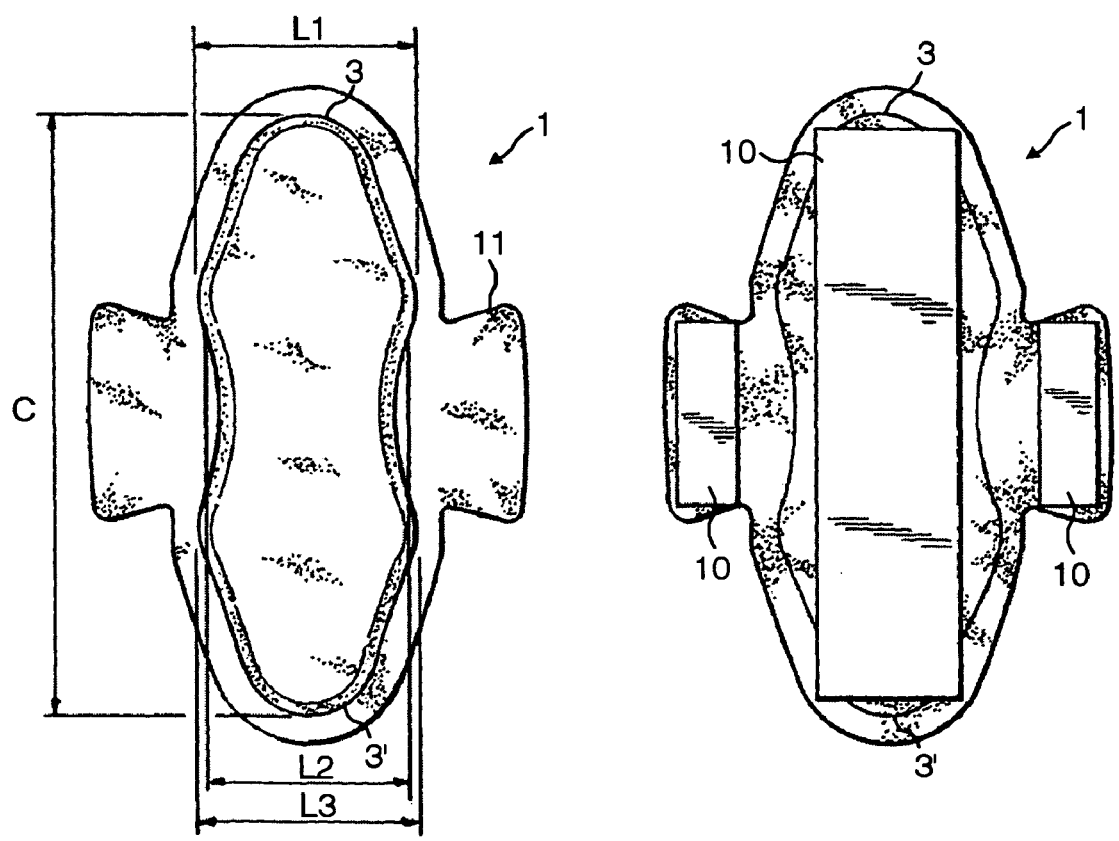
FIG. 2—is a top view of the napkin illustrated in FIG. 1.
FIG. 3—is a bottom view of the napkin illustrated in FIGS. 1 and 2.

According to a first embodiment as shown in FIG. 1, the sanitary napkin 1 of this invention comprises a substantially planar and elongated absorbent portion 2, which forms a main body or chassis of napkin. The absorbent portion 2 comprises a liquid pervious material layer, a liquid impervious material layer and an absorbent core between the liquid pervious material layer and the liquid impervious material layer. The absorbent portion 2 has a first main end 3, from which it extends to a second main end 3'. The absorbent portion also has a first longitudinal side and an opposite second longitudinal side. The total length C of the absorbent portion 2 is the distance between the first main end 3 and the second main end 3'. The absorbent portion has a varying width along its length. The width is measured as the distance between the first longitudinal side edge and the second longitudinal side edge along a line that is perpendicular to an imaginary longitudinal centerline, i.e. is substantially perpendicular to the length C of the absorbent portion 2. The length C has a value greater than any of the widths of the absorbent portion 2 hereinafter described. The absorbent portion 2 has a maximum width L1, (herein after referred to as a first width) located between ⅕ and ½ of the length C value of the absorbent portion 2 measured from the first transverse end 3, preferably this width L1 being located at about ⅓ of said length C value. The value of L1 is greater than any width of the absorbent portion 2 in the region between the first transverse end 3 and L1. The region between L1 and the first transverse end 3 is less than L1 and preferably constantly tapers from L1 to the first transverse end 3, as shown in FIG. 1. Accordingly, the width of the absorbent portion 2 increases between the first main end 3 (where this value is zero) and the distance between ⅕ and ½ from the of the longitudinal length thereof, where the width is maximum. Preferably, but not obligatorily, the width increases linearly with respect to the increase of the distance between the first transverse end 3 and the distance between ⅕ and ½ of the of the longitudinal length C. The absorbent portion 2 has a second width L2 located at ⅕ to ½ of the length C value of the absorbent portion 2 measured from the second transverse end 3. The value of the L2 is less than or equal to the L1 value. The value of L2 is greater than any value of the absorbent portion 2 width between the second transverse end 3 and the distance between ⅕ and ½ of the longitudinal length C thereof. The absorbent portion 2 also has a central region intermediate the first width L1 and the second width L2, the central region having a maximum width L3 that is less than or equal to the first width L1. In a preferred embodiment, L1 and L2 are substantially equal, L3 is less than L1 and L2 and the longitudinal side edges of the absorbent portion 2 in the central region are arcuate, in a convex inward orientation to form an hourglass shaped structure. That is, the absorbent portion 2 has its end edges of substantially curved shape in its central region, the centers of the curvature radiuses of the edges being located substantially externally to the absorbent portion 2, in such a manner that this central region is substantially anatomic, providing an optimized fit in the region between the user's legs and a soft movement of her legs, providing use comfort and the sensation of not being using the sanitary napkin.

Such constructive arrangement features a central region more anatomic, and the narrower ends result in lesser deformation of the product in use due to the material reduction in these regions, which gives the required protection with more comfort and discretion. Moreover, this invention presents as advantages the fact of providing a sanitary napkin having a central region more anatomic and narrower ends, which results in lesser deformation of the product in use due to the material reduction in these regions and provides the required protection with more comfort and discretion. This feature can characterize two ends or the first transverse end 3 of the napkin 1 only.

In the case of two ends of the absorbent portion 2 have this geometric construction, the first and second main ends 3, 3' are indistinct, and the length values of the portion 2 can be taken from any of these ends 3, 3'.

A first version of sanitary napkin comprises a liquid pervious material layer 4, the inner surface of which is joined by construction adhesive 5 to a first surface of a transfer layer 6, the second surface of which, in turn, is joined to a first surface of an absorbent core (that is capable of absorbing liquid exudate) 7, which has its second surface joined to a first surface, or inner surface, of a liquid impervious material layer as a liquid impervious plastic film 8, also by means of the construction adhesive 5. Any conventional liquid pervious materials, liquid impervious materials, transfer layers and absorbent materials that are well known in the art are suitable for use in the present invention.

The liquid pervious layer may be formed from any flexible, liquid permeable material that is non-irritating to a user. Suitable liquid permeable materials include, but are not limited to woven fabrics, non-woven fabrics, apertured plastic films, and the like. The liquid pervious layer is preferably a relatively low density, bulky, high-loft non-woven web material. The liquid pervious layer may be composed of only one type of fiber, such as polyester or polypropylene or it may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof.

The liquid pervious layer preferably has a relatively high degree of weltability, although the individual fibers used to form this layer may not be particularly hydrophilic. The liquid pervious layer material should also contain a great number of relatively large pores. This is because the liquid pervious layer is intended to take-up body fluid rapidly and transport it away from the body and the point of deposition. Advantageously, the fibers which make up the liquid pervious layer should not lose their physical properties when they are wetted, in other words they should not collapse or lose their resiliency when subjected to water or body fluid. The liquid pervious layer may be treated to allow fluid to pass through it readily. The liquid pervious layer also functions to transfer the fluid quickly to the other layers of the absorbent system. Thus, the liquid pervious layer is advantageously wettable, hydrophilic and porous. When composed of synthetic hydrophobic fibers such as polyester or bi-component fibers, the liquid pervious layer may be treated with a surfactant to impart the desired degree of wettability. An alternative embodiment would be that the liquid pervious layer is composed of an apertured film.

The liquid pervious layer may be affixed, e.g., by embossing to the remainder of the absorbent system by affixing the liquid pervious layer to the underlying layer in order to assist fluid transport from the liquid pervious layer to the absorbent system. Such affixation may be effected locally, at a plurality of sites or over the entire contact surface of the liquid pervious layer absorbent system. Exemplary means of affixing the liquid pervious layer to the absorbent system are adhesion and fusion.

The transfer layer 6 may be composed of fibrous materials, such as wood pulp, polyester, rayon, or the like, or combinations thereof. In a preferred embodiment, the transfer layer 6 is composed of fibrous materials and may include thermoplastic fibers for the purpose of stabilizing the layer and maintaining its structural integrity. The transfer layer 6 may be treated with surfactant on one or both sides in order to increase its wettability, although generally the transfer layer 6 is relatively hydrophilic and may not require treatment. The transfer layer 6 is preferably bonded on both sides to the adjacent layers, i.e. the liquid pervious layer and an underlying liquid impervious layer.

Materials particularly suitable for use in the transfer layer 6 have an open cellular structure that is capable of rapidly acquiring liquid and generally have a density in the range of about 0.04 to 0.05 g/cc, a basis weight in the range from about 80 to 110 g/m$^2$ and a thickness in the range of less than about 1 to 3 mm. Examples of suitable materials for the transfer layer 6 are through air bonded pulp sold by Buckeye of Memphis, Tenn., under the designation VIZORB 3008, which has a basis weight of 110 g/m$^2$ and VIZORB 3010, which has a basis weight of 90 g/m$^2$.

Immediately subjacent to and bonded to the transfer layer 6 is the absorbent core 7. In a preferred embodiment, the absorbent core 7 is a blend or mixture of cellulosic fibers and superabsorbent disposed in and amongst fibers of that pulp.

In a specific example, the absorbent core 7 is a material containing from about 40 weight percent to about 95 weight percent cellulosic fibers and, more specifically from about 60 to about 80 weight percent cellulosic fibers. Such a material may contain from about 5 weight percent to about 60 weight percent SAP (superabsorbent polymers), preferably form about 20 to about 55 weight SAP, and even more preferably from about 30 to 45 weight percent SAP, and most preferably about 40 weight percent SAP. The material has a water content of less than about 10 weight percent. As used herein, the phrase "weight percent" means weight of substance per weight of final material. By way of example, 10 weight percent SAP means 10 g/m² SAP per 100 g/m² basis weight of the material.

Cellulosic fibers that can be used in the absorbent core 7 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material.

The absorbent core 7 can contain any superabsorbent polymer (SAP), which SAPs are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The partides may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA60N Type II*, the product offered by Stockhausen, Inc. of Greensboro, N.C., under the designation of 7440, and the product offered by Chemdal International, Inc. of Palatine, Ill., under the designation of 2100A*.

The absorbent core 7 can be manufactured by using air-laying means. In accordance with this process cellulosic fibers (e.g., pulp) are processed using a hammer mill to individualize the fibers. The individualized fibers are blended with SAP granules in a blending system and pneumatically conveyed into a series of forming heads. The blending and distribution of fibers and SAP granules can be controlled separately for each forming head. Controlled air circulation and winged agitators in each chamber produce uniform mixture and distribution of pulp and SAP. The SAP can be thoroughly and homogeneously blended throughout the material or contained only in specific strata by distributing it to selected forming heads. Fibers (and SAP) from each forming chamber are deposited by vacuum onto a forming wire thus forming a layered absorbent web. The web is subsequently compressed using calendars to achieve desirable density. The densified web is wound into a roll using conventional winding equipment. The forming wire can be covered with tissue paper to reduce the loss of material. The tissue paper layer can be removed prior to calendering or incorporated into the formed material. In a possible variant, the transfer layer can be formed integrally with the absorbent core 7 to provide a unitized absorbent system.

The absorbent core 7 is perferably of high density and preferably has a density of greater than about 0.25 g/cc. In general, the absorbent core 7 has a density in the range of from about 0.25 g/cc to about 0.50 g/cc., more preferably from about 0.25 g/cc to about 0.40 g/cc and most preferably from about 0.25 g/cc to about 0.35 g/cc.

Air-laid absorbents are typically produced with a low density. To achieve higher density levels, such as the examples of the absorbent core 7 given above, the air-laid material is compacted using calenders. Compaction is accomplished using means well known in the art. Typically such compaction is carried out at a temperature of about 100 degrees C. and a load of about 130 Newtons per millimeter.

The absorbent core 7 can be prepared over a wide range of basis weights. The absorbent core 7 can have a basis weight in the range of from about 100 g/m² to about 700 g/m². In a specific example, the basis weight ranges from about 150 g/m² to about 400 g/m². Preferably the basis weight ranges from about 200 g/m² to about 350 g/m² and, more preferably, to about 250 g/m².

The transfer layer 6 functions to rapidly absorb and retain fluid which is then more slowly absorbed by the absorbent core 7. The transfer layer 6 having a relatively open pore structure readily absorbs and disperses liquid laterally within its bulk and readily transfers the liquid to the receiving surface of the absorbent core. In turn, the absorbent core having a relatively smaller pore structure than the transfer layer 6 has good capillarity which efficiently draws liquid into its bulk from the transfer layer 6. Once the liquid has been absorbed into superabsorbent polymer, the liquid cannot be subsequently released by applying pressure. Therefore, the liquid absorbed into the superabsorbent material becomes entrapped. At the same time, the strength with which absorbent core 7 intakes liquid from the transfer layer 6 helps to reduce the proportion of liquid held in the transfer layer 6, thereby reducing the amount of liquid that returns to the liquid pervious layer when the napkin is subjected to mechanical loading. Furthermore, the transfer layer 6 has a relatively high capillarity so that any concentration of liquid in the transfer layer 6 resulting from mechanical loading can be redistributed within the material to lower concentrations, again reducing the amount of liquid which can return to the liquid pervious layer.

In a specific embodiment, the absorbent core 7 contains in the range from about 30 to 40 weight percent superabsorbent material, has a basis weight in the range from about 200 to 400 g/m² and a density in the range from about 0.2 to 0.5 g/cc. More specifically, the density is from about 0.25 g/cc to about 0.45 g/c and, even more specifically about 0.3 g/cc.

The absorbent core 7 can be formed as three or four lamina or strata. Those strata include a bottom layer, one or two middle layers and a top layer. Specific examples of three and four layer material are set forth below. The SAP can be included in any or all of the layers. The concentration (weight percent) of SAP in each layer can vary as can the nature of the particular SAP.

Even where prepared as from multiple layers, the final thickness of the formed absorbent core 7 is preferably low. The thickness can vary from less than about 0.5 mm to about 2.5 mm. In a specific example, the thickness is from less than about 0.5 mm to about 1.5 mm.

Underlying the absorbent system is a layer of a liquid impervious material so as to prevent liquid that is entrapped in the absorbent system from egressing the sanitary napkin and staining the wearer's undergarment. The liquid impervious layer is preferably made of polymeric film, although it may be made of liquid-impervious air-permeable material such as repellent-treated, non-woven or microporous films or foams.

The liquid pervious layer and the liquid impervious layer are joined along their marginal portions so as to form an enclosure or flange seal that forms a unitary absorbent product and maintains the absorbent system captive. The joint may be made by means of adhesives, heat-bonding, ultrasonic bonding, radio frequency sealing, mechanical crimping, and the like and combinations thereof.

Optionally, projecting laterally outward from each of the longitudinal sides is a flap 11. The flap 11 is in the shape of an isosceles trapezoid with the top adjoining the longitudinal side and the base at the distal end. The flap 11 is preferably made as integral extensions of the liquid pervious layer and the liquid impervious layer. These integral extensions are joined to one another along their marginal seal portions by adhesives, heat-bonding, ultrasonic bonding, radio frequency sealing, mechanical crimping, and the like and combinations thereof. Most preferably, such joining is made at the same time the liquid pervious layer and the liquid impervious layer are bonded to one another to enclose the absorbent system. Alternatively, the flaps may include absorbent material between the liquid pervious layer and the barrier layer extensions. Such absorbent material may be an extension of the transfer layer 6, the absorbent core 7 or both.

Finally, there is a central positioning adhesive 9 of the napkin 1 in the user's undergarment (not shown), positioned in a second surface, or outer surface, of the film 8, and protected by a protector material sheet 10, which must be removed when the napkin 1 is used. Optionally, in the case of the napkin having flap 11, it further comprises at least one flap 9' positioning adhesive layer covered by a protector material sheet 10' analogous to that described above.

A second version of absorbent napkin comprises a layer of absorbent compound 7' significantly thicker than that haven in the first version, which occupies the place of the transfer layer 6 and the thin absorbent compound 7. These are the only differences with respect to the first version explained above.

Optionally, the absorbent portion may be provided with embossed channels 12, like designs obtained by means of channels 12 made throughout the absorbent core to direct liquid along the channel (or channels) for subsequent absorption into the transfer layer 6. The channels are formed by applying localized pressure to the absorbent material, such pressure as for example is conventionally used in embossing. The applied pressure results in densifying the absorbent material which defines the floor of the channel rendering it less pervious to liquid and so extending the distance over which the liquid can travel before absorption. It has been found that the provision of channels contributes significantly to the stability of the napkin in use and also the potential of the napkin to retain fluid in contact with a wearer's body, often referred to as a rewet potential. In addition, the provision of one or more channels adjacent the liquid pervious layer enables liquid to be transported rapidly over the napkin so that different regions of the transfer layer 6 act effectively to absorb the liquid in parallel. This helps to ensure that liquid is presented to a larger portion of the surface area of the absorbent core 7 to increase the effectiveness of the absorbent core 7 in drawing liquid from the transfer layer 6. Preferably, the napkin has a plurality of elongate channels formed therein, which are spaced apart from each other and configured to channel liquid laterally across the body-facing surface of the napkin or near body facing surface portion thereof, away from the region of initial deposition.

In a preferred embodiment, the sanitary napkin is provided with at least one and preferably more than one channel, for example running along or parallel to the longitudinal axis along the length of the napkin, obliquely of the longitudinal axis, for example from one side of the napkin to the other or substantially perpendicular to the longitudinal axis. The channel(s) may have any shape which may be selected according to the particular application, for example the channels may be linear, arcuate or have a serpentine configuration or a mixture of these as well as other shapes, including a spiral and zigzag patterns.

Figure 4:
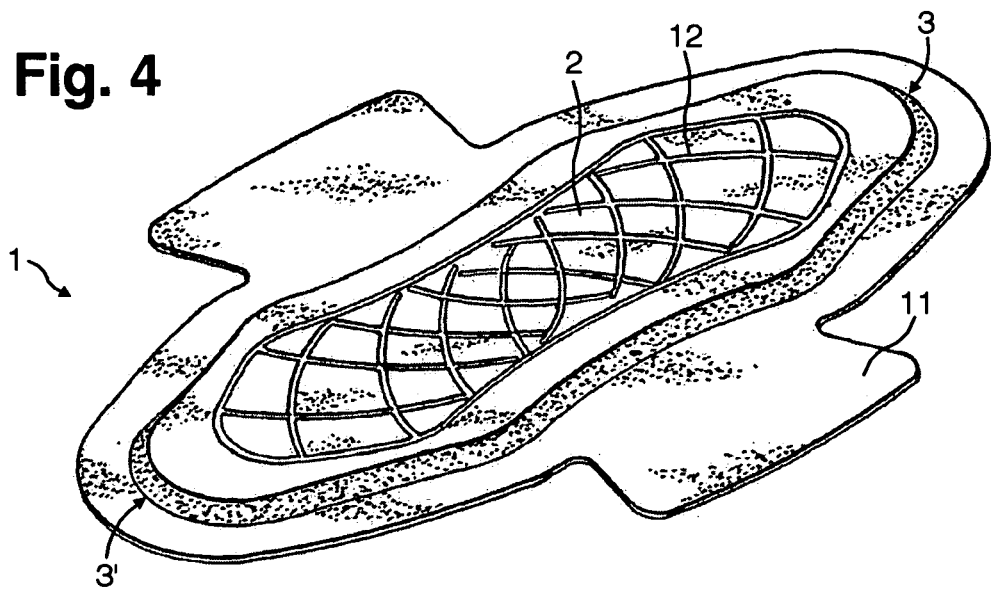
FIG. 4—is a perspective view of a second variation of the sanitary napkin object of this invention.
Figure 5:
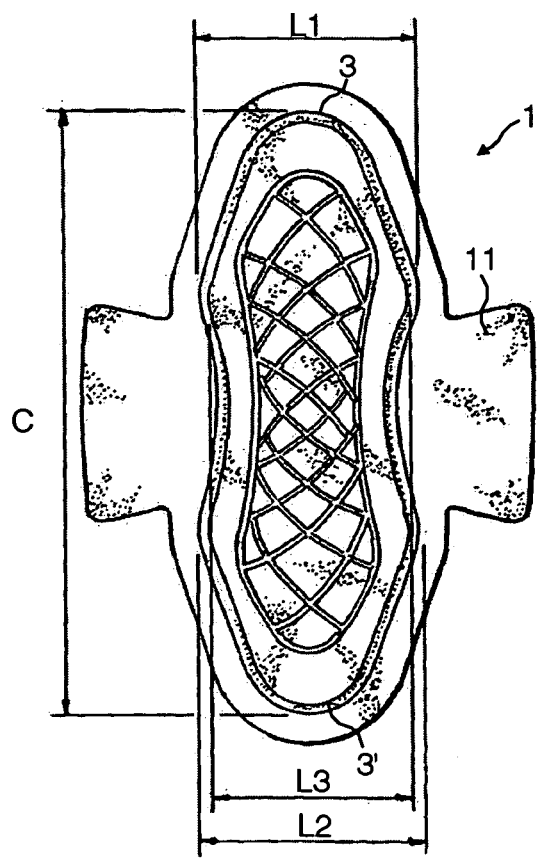
FIG. 5—is a top view of the napkin illustrated in FIG. 4.
Figure 6:
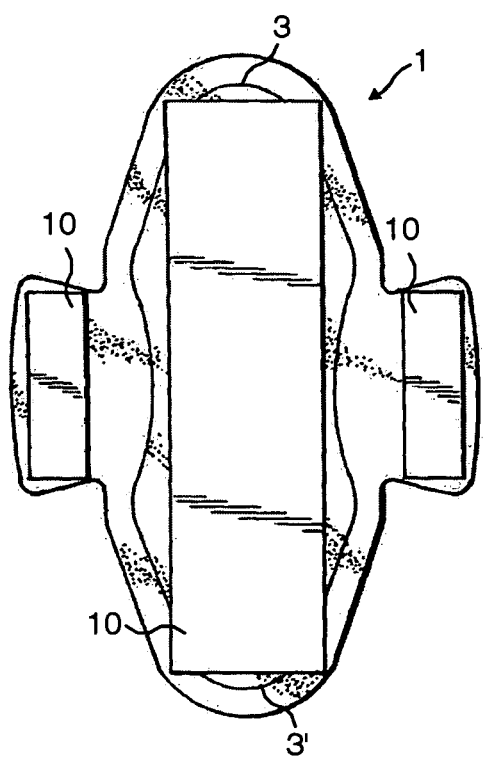
FIG. 6—is a bottom view of the napkin illustrated in FIGS. 4 and 5.
Figure 10:
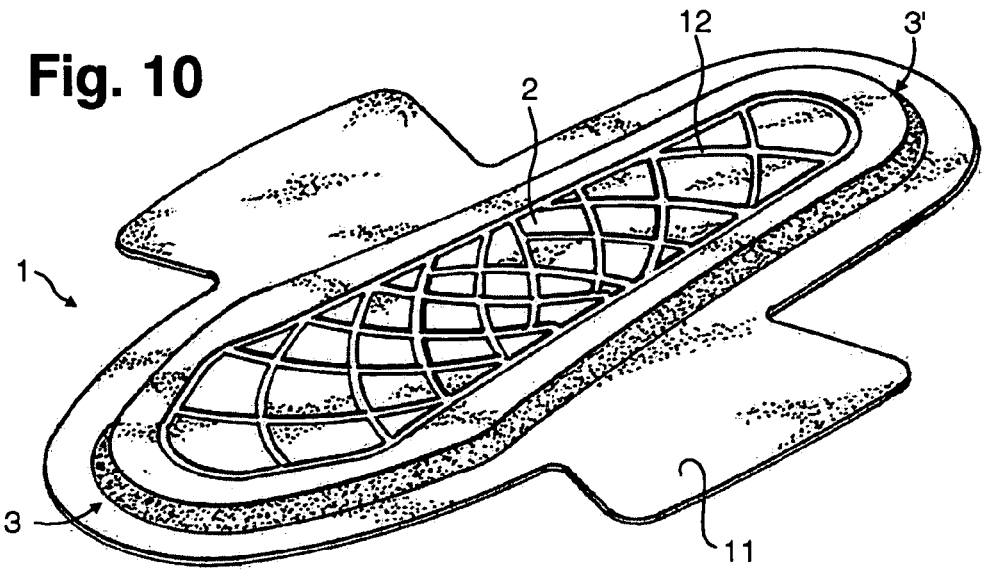
FIG. 10—is a perspective view of a fourth variation of the sanitary napkin object of this invention.
Figures 11, 12:
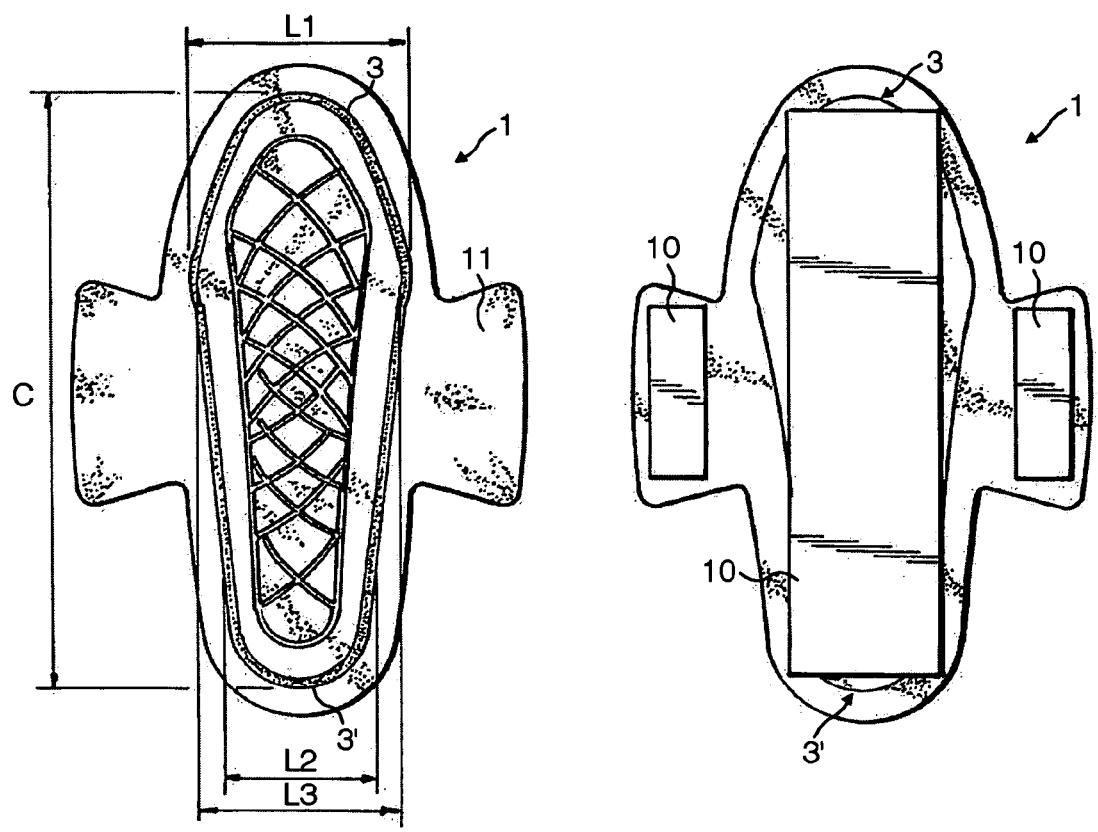
FIG. 11—is a top view of the napkin illustrated in FIG. 10.
FIG. 12—is a bottom view of the napkin illustrated in FIGS. 10 and 11.
Figure 13:
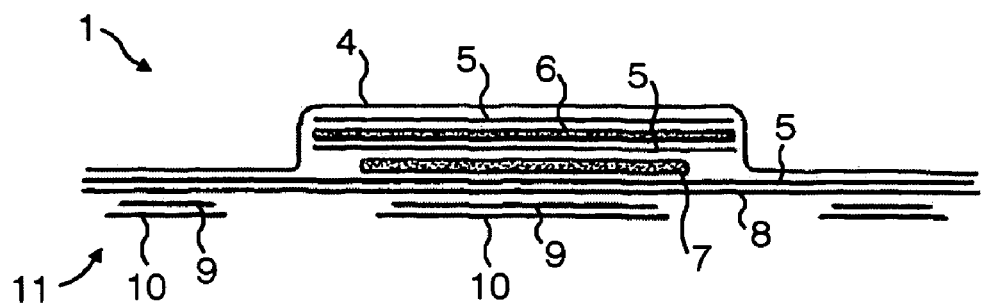
FIG. 13—is a schematic cut view of a first version of first and third variations of the sanitary napkin object of this invention.
Figure 14:
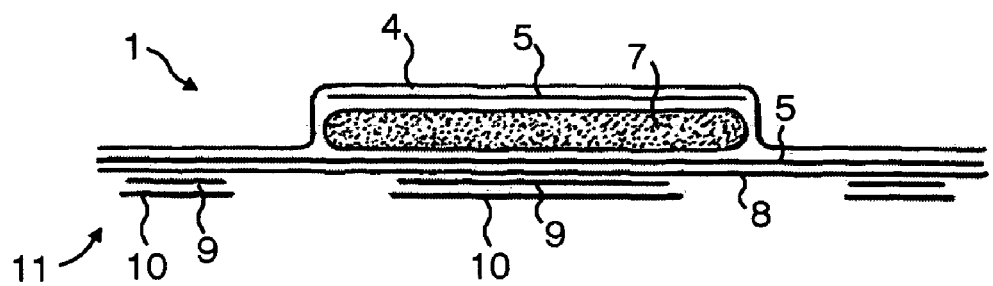
FIG. 14—is a schematic cut view of a second version of first and third variations of the sanitary napkin object of this invention.
Figure 15:
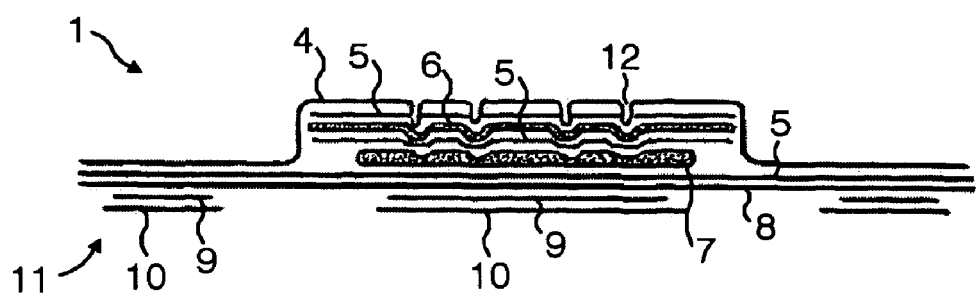
FIG. 15—is a schematic cut view of a first version of second and fourth variations of the sanitary napkin object of this invention.
Figure 16:
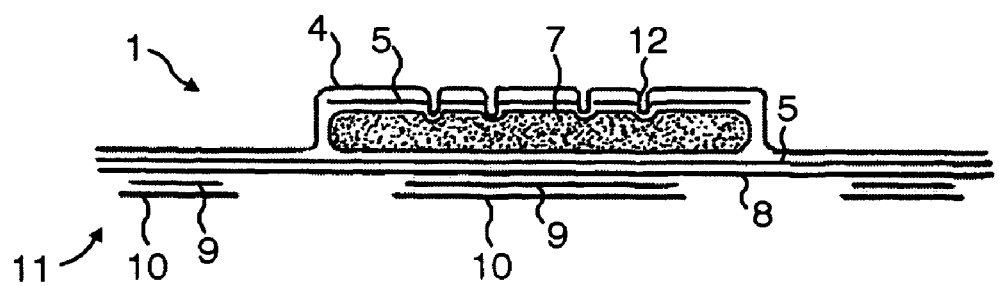
FIG. 16—is a schematic cut view of a second version of second and fourth variations of the sanitary napkin object of this invention.

In one embodiment, the napkin has a plurality of discrete channel formations which are spaced apart and intersect one another. An example of such an embodiment is shown in FIGS. 4 and 5. Referring to these Figures, the absorbent portion 2 is provided with a plurality of arcuate channels 12 which extend generally obliquely with respect to a longitudinal center line and extend from one side of the napkin surface across the center of the napkin to the other side. This design not only stabilizes the napkin against deformation caused by lateral compressive forces but also efficiently conducts liquid simultaneously along the length and across the width of the napkin. The channel formation may be formed in the liquid pervious layer and/or in the transfer layer 6. Advantageously, the absorbent portion may optionally comprise thermoplastic fibers. The provision of thermoplastic fibers assists in the formation of a stable and permanent channel when the thermoplastic fibers are subjected to heat. When heat is applied, the thermoplastic fibers tend to fuse together to form a more rigid structure so that the original form of the channels is maintained during use and over time. Conveniently, the application of heat may be incorporated with the embossing process.

One can even utilize the absorbent portion of this invention in other absorbent products, such as diapers for newly-born children or for geriatric utilization, or other similar absorbent products.

Since it has been described an example of preferred embodiment, it shall be understood that the scope of this invention encompasses other possible variations, being limited only by the contents of the appended claims, included therein the possible equivalents.

What is claimed is:

1. A sanitary napkin adapted to be worn in a crotch portion of a user's undergarment for the absorption of body exudate, comprising an absorbent portion having a first transverse end and an opposite second transverse end defining therebetween a length, a first longitudinal side and an opposite second longitudinal side defining therebetween a width, the width varying along the length of the absorbent portion, wherein:

(i) a first width is located between $1/5$ and less than $1/2$ of the length of the absorbent portion as measured from the first transverse end, the first width being greater than any width of the absorbent portion located between the first transverse end and the first width;

(ii) a second width located substantially from $1/5$ to less than $1/2$ of the length of the absorbent portion as measured from the second transverse end, the second width being less than or equal to the first width;

(iii) a central region intermediate the first width and the second width, the central region having a maximum width that is less than or equal to the first width;

wherein the absorbent portion has a plurality of elongate embossed channels, each channel being spaced apart from an adjacent channel and extending obliquely with respect to a longitudinal axis from one side of the napkin to an opposite side of the napkin.

2. A sanitary napkin, according to claim 1, wherein the first width is located at $1/3$ of the length of the absorbent portion as measured from the first transverse end.

3. A sanitary napkin, according to claim 1 wherein the central region has a maximum width that is less than the first width an the second width is less than the first width.

4. A sanitary napkin according to claim 1, wherein the width of the absorbent portion increases linearly between the first transverse end and the first width.

5. A sanitary napkin according to claim 1 wherein the first width and the second width are substantially equal and the longitudinal sides of the absorbent portion have a substantially curved shape in the central region, the absorbent portion having a substantially hour-glass shape.

6. A sanitary napkin according to claim 1 wherein the central region has a maximum width that is less than the first width an the second width is less than the first width, the first longitudinal side and the opposite second longitudinal side converging towards each other as they approach the second transverse end.

7. A sanitary napkin according to claim 1 wherein the second width is greater than any width of the absorbent portion located between the second transverse end and the second width, the second width being substantially equal to the first width.

* * * * *